United States Patent
Goddard et al.

(10) Patent No.: US 8,870,743 B2
(45) Date of Patent: Oct. 28, 2014

(54) PELVIC FLOOR MESH AND INCONTINENCE SLING

(75) Inventors: James Goddard, Pepperell, MA (US); Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 620 days.

(21) Appl. No.: 12/412,951

(22) Filed: Mar. 27, 2009

(65) Prior Publication Data

US 2010/0081866 A1    Apr. 1, 2010

Related U.S. Application Data

(60) Provisional application No. 61/043,214, filed on Apr. 8, 2008.

(51) Int. Cl.
*A61F 2/00* (2006.01)

(52) U.S. Cl.
CPC ............. *A61F 2/0045* (2013.01); *A61F 2/0063* (2013.01)
USPC .......................................................... 600/37

(58) Field of Classification Search
USPC ................. 600/29–32, 37; 128/885; 606/151; 604/329; 623/17.11
See application file for complete search history.

(56) References Cited

U.S. PATENT DOCUMENTS

| | | | |
|---|---|---|---|
| 5,824,082 A | 10/1998 | Brown | |
| 6,669,706 B2 | 12/2003 | Schmitt et al. | |
| 6,669,735 B1 | 12/2003 | Pelissier | |
| 6,953,428 B2 | 10/2005 | Gellman et al. | |
| 7,070,558 B2 | 7/2006 | Gellman et al. | |
| 7,717,892 B2* | 5/2010 | Bartning et al. | 604/329 |
| 2003/0069469 A1* | 4/2003 | Li | 600/30 |
| 2005/0250978 A1 | 11/2005 | Kammerer | |
| 2006/0282105 A1* | 12/2006 | Ford et al. | 606/151 |
| 2007/0088189 A1* | 4/2007 | Levy | 600/37 |
| 2007/0156012 A1* | 7/2007 | Tracey et al. | 600/30 |
| 2007/0265710 A1* | 11/2007 | Brown et al. | 623/23.72 |
| 2007/0276494 A1* | 11/2007 | Ferree | 623/17.11 |
| 2008/0161837 A1* | 7/2008 | Toso et al. | 606/151 |
| 2008/0281149 A1* | 11/2008 | Sinai et al. | 600/32 |

FOREIGN PATENT DOCUMENTS

| | | |
|---|---|---|
| WO | 2007/087146 A2 | 8/2007 |
| WO | WO 2007/087146 A2 | 8/2007 |
| WO | 2008/015722 A1 | 2/2008 |
| WO | WO 2008/015722 A1 | 2/2008 |
| WO | 2009/005714 A2 | 1/2009 |
| WO | WO 2009/005714 A2 | 1/2009 |

OTHER PUBLICATIONS

International Preliminary Report on Patentability for PCT Application No. PCT/US2009/038918, mailed on Oct. 21, 2010, 11 pages.

(Continued)

*Primary Examiner* — Christine Matthews

(57) ABSTRACT

A support device includes a support member and a frame member. The support member has a body portion and an elongated arm extending from the body portion. The elongated arm has a width smaller than a width of the body portion of the support member. The body portion is configured to help support an anatomical structure located in a pelvic region of a patient. The frame member is coupled to the support member and comprised of a shape memory alloy.

18 Claims, 5 Drawing Sheets

(56) References Cited

OTHER PUBLICATIONS

Rebound HRD™ Product Information Sheet [online], [retrieved on Apr. 3, 2007], Retrieved from the Internet<URL: http://www2mdinc.com/Products/products.html.

International Search Report and Written Opinion for International Application No. PCT/US2009/038918, mailed on Jun. 23, 2009, 15 pages.

Communication pursuant to Article 94(3) EPC for EP Application No. 09729598.4, mailed Feb. 7, 2014, 6 pages.

* cited by examiner

PELVIC FLOOR MESH AND INCONTINENCE SLING

CROSS-REFERENCE TO RELATED APPLICATION

This application claims priority to U.S. Provisional Patent Application Ser. No. 61/043,214, entitled "Pelvic Floor Mesh and Incontinence Sling," filed Apr. 8, 2008, the disclosure of which is incorporated herein by reference in its entirety.

BACKGROUND

This invention relates to a medical device and more particularly to a medical device configured to be placed within a pelvic floor region of a patient.

The disclosed embodiments have applications to a wide variety of medical procedures. For example, one such procedure is directed to insertion of a support device into a pelvic floor region of a patient to support an anatomical structure. Known support devices have multiple sutures or anchors configured to fix a support (e.g., a filament, a sling, or a mesh) at spaced locations while retaining the support between them to provide support for other portions of the body. Such a support device damages tissue during insertion and removal of each of the sutures or tissue anchors.

A need exists for a support device that is configured to be placed within and retained within the pelvic floor region of a patient without the need for sutures or other tissue anchoring devices.

SUMMARY OF THE INVENTION

In one embodiment, a support device has a body portion and an elongated arm extending from the body portion. The elongated arm has a width smaller than a width of the body portion of the support member. The body portion is configured to help support an anatomical structure located in a pelvic floor region of a patient. A frame member is coupled to the support member and is comprised of a shape memory alloy.

In another embodiment, a support member has an expanded configuration and a collapsed configuration. The support device is configured to support tissue within the pelvic region when the support member is in the expanded configuration. The support member has a first side portion and a second side portion opposite the first side portion. A first elongated arm extends from the first side portion of the support member. A second elongated arm extends from the second side portion of the support member. The first elongated arm and the second elongated arm are disposed in an adjacent arrangement when the support member is in the collapsed configuration. A frame member is coupled to the support member.

In yet another embodiment, a plurality of interwoven strands collectively define a shape. A strand is interwoven into the plurality of interwoven strands. The strand includes a shape memory alloy. The strand has a biased first configuration and a second configuration different from the first configuration. The strand is configured to retain the plurality of interwoven strands in an expanded configuration such that the support device defines a shape configured to support a bodily structure.

BRIEF DESCRIPTION OF THE DRAWINGS

The present invention is described with reference to the accompanying drawings.

DETAILED DESCRIPTION

The medical devices described herein can be inserted and placed into a body of a patient. For example, the medical support device can be placed within a body of a patient to support an anatomical structure such as a bladder. For example, the medical support device can have elongated arms to help retain the support device at a location with respect to the anatomical structure to be supported.

Figure 1:
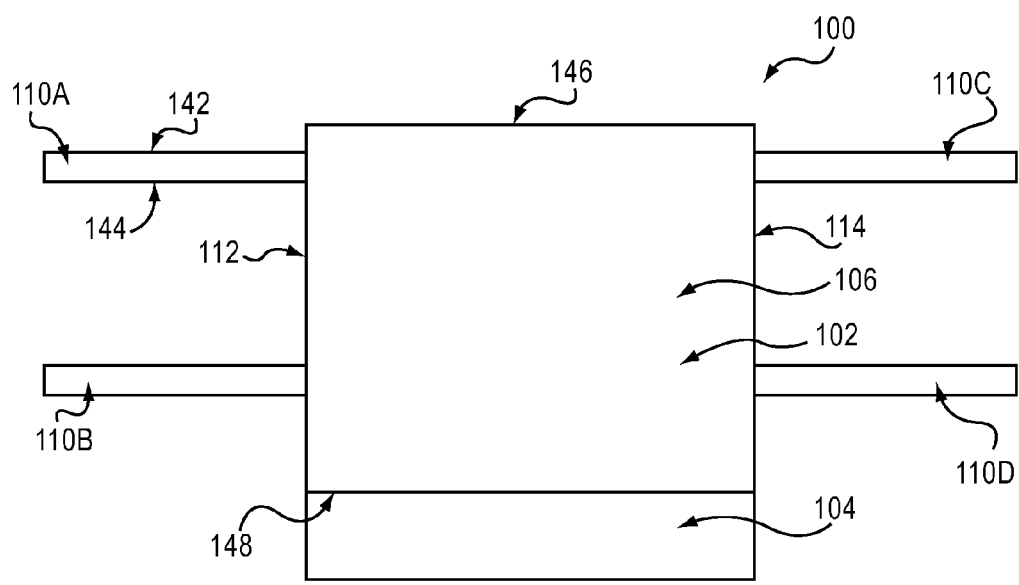
FIG. 1 is a schematic illustration of an embodiment of a support device.

FIG. 1 is a schematic illustration of an embodiment of a support device. An apparatus 100 (also referred to herein as "support device") can be placed or otherwise inserted into a body of a patient, such as, for example, within a pelvic floor region of the body.

The support device 100 includes a support member 102 and a frame member 104. The support member 102 has a body portion 106 and multiple elongated arms 110A, 110B, 110C, 110D extending from the body portion 106. Specifically, the support member 102 has a first side portion 112 and a second side portion 114 opposite the first side portion 112. A first elongated arm 110A and a second elongated arm 110B extend from the first side portion 112 of the support member 102. A third elongated arm 110C and a fourth elongated arm 110D extend from the second side portion 114 of the support member 102. The elongated arms 110A, 110B, 110C, 110D have a width smaller than a width of the body portion 106 of the support member 102. The width of the body portion 106 is sufficient to help support an anatomical structure in the pelvic floor.

The support member 102 has an expanded configuration and a collapsed configuration. The body portion 106 is configured to help support the anatomical structure or tissue located in the pelvic floor region of the patient when the support member 102 is in the expanded configuration. The elongated arms 110 are configured to help retain the support member 102 at a location with respect to the anatomical structure when the support member 102 is in the expanded configuration.

The support device 100 is configured to facilitate insertion into the pelvic floor region when the support member 102 is in the collapsed configuration. Specifically, in one embodiment, the support member 102 is configured to be slidably inserted into a lumen of an insertion device (not shown) when the support member 102 is in the collapsed configuration. More specifically, the first elongated arm 110A, the second elongated arm 110B, the third elongated arm 110C and the fourth elongated member 110D are disposed in an adjacent arrangement when the support member 102 is in the collapsed configuration and oriented such that the elongated arms 110 are disposed within a distal end portion of the lumen of the insertion device.

Adjacent arrangement, as used herein, can be, for example, when the elongated arms 110 are closer to one another when the support member 102 is in the collapsed configuration than the elongated arms 110 are when the support member 102 is in the expanded configuration. For example, each elongated arm 110 can be immediately adjacent to another arm without intervening space when in the adjacent arrangement.

The frame member 104 is fixedly coupled to the support member 102 and configured to help retain a shape defined by the support member 102 when the support member 102 is in the expanded configuration such that the shape facilitates the body portion 106 in supporting the anatomical structure. In some embodiments, the frame member 104 is coupled to the elongated arms 110. The frame member 104 is comprised of a shape memory alloy, such as, for example, nitinol, gold-cadmium, nickel-aluminum, manganese-copper, or the like. Specifically, the frame member 104 is configured to return to the predefined shape when the shape is deformed or not in the predefined shape.

In one embodiment, the support member 102 includes multiple interwoven strands. A shape memory strand is interwoven into the multiple interwoven strands and includes a shape memory alloy. The shape memory strand has a biased first configuration and a second configuration different from the biased first configuration. The shape memory strand is configured to move from the second configuration to the biased first configuration such that the multiple strands collectively define the shape configured to support the anatomical structure (i.e., a bodily structure).

Although FIG. 1 illustrates one frame member 104, in some embodiments, the support device 100 includes a second frame member coupled to the support member 102. In some embodiments, the support member 102 is a mesh or mesh-like material. In some embodiments, the support member 102 has an "I"-shape or an "H"-shape. In some embodiments, the support member 102 includes multiple interwoven strands. In some embodiments, the support member 102 includes a single elongated arm.

In one embodiment, the body portion 106 has a first side portion 146 and a second side portion 148 opposite the first side portion 146. Each of the elongated arms 110 of the support member 102 has a first side portion 142 and a second side portion 144 opposite the first side portion 142. The distance between the first side portion 142 of the elongated arms 110 and the second side portion 144 of the elongated arms 110, respectively, is smaller than a distance between the first side portion 146 of the body portion 106 and the second side portion 148 of the body portion 106.

Figure 2:
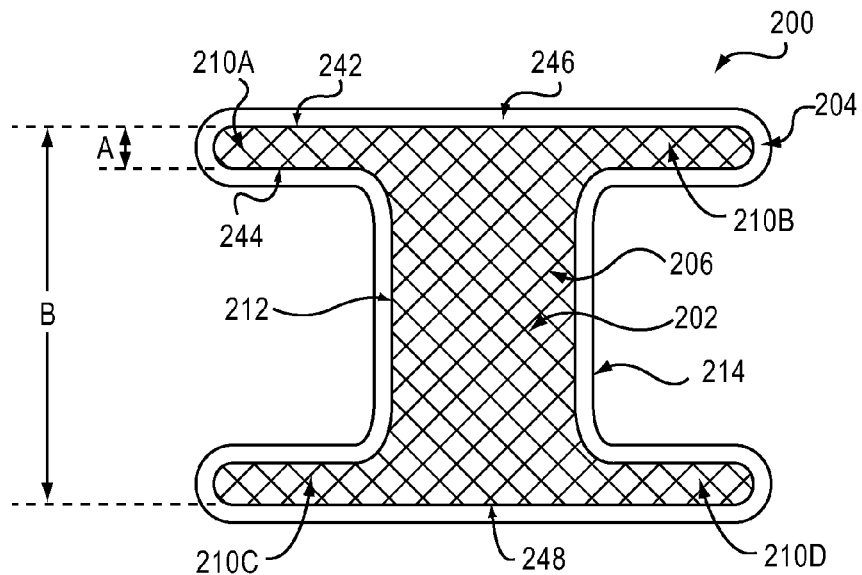
FIG. 2 is a top view of an embodiment of a support device in an expanded configuration.

FIG. 2 is a top view of an embodiment of a support device 200. The support device 200 includes a support member 202 and a frame member 204. The support member 202 has a body portion 206 and multiple elongated arms 210A-D each extending from the body portion 206. The body portion 206 is configured to help support a tissue or an anatomical structure located in a pelvic region of a patient.

Figure 3:
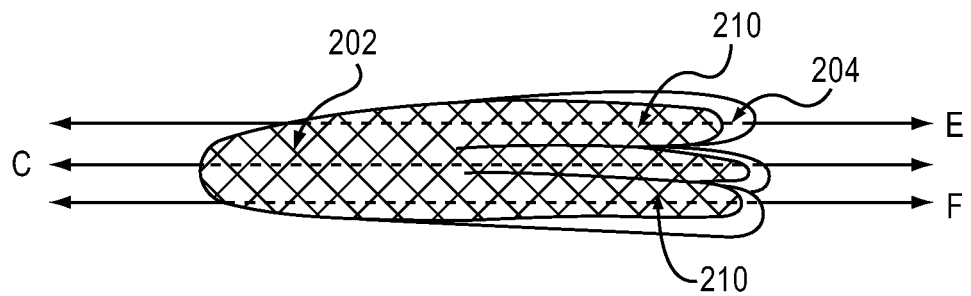
FIG. 3 is a side view of the support device of FIG. 2 in a collapsed configuration.

The support member 202 has an expanded configuration as shown in FIG. 2 and a collapsed configuration as shown in FIG. 3. The support device 200 is configured to support the anatomical structure when the support member 202 is in the expanded configuration. The support device 200 is configured to facilitate insertion of the support device 200 into the pelvic region when the support member 202 is in the collapsed configuration.

The support member 202 has a first side portion 212 and a second side portion 214 opposite the first side portion 212. A first elongated arm 210A and a second elongated arm 210C extend from the first side portion 212 of the support member 202. A third elongated arm 210B and a fourth elongated arm 210D extend from the second side portion 214 of the support member 202. Each of the elongated arms 210A, 210B, 210C, 210D is configured to help retain the support member 202 at a location in the pelvic floor with respect to the anatomical structure that is being supported when the support member 202 is in the expanded configuration. The elongated arms 210A-D are disposed in an adjacent arrangement when the support member 202 is in the collapsed configuration.

Each of the elongated arms 210A-D has a maximum width A that is smaller than a maximum width B of the body portion 206 of the support member 202. In the illustrated embodiment, the width B of the body portion 206 is sufficient to help support the anatomical structure when the support device 200 is disposed in a body of a patient. In other words, each elongated arm 210A-D has a first side portion 242 and a second side portion 244 opposite the first side portion 242. The body portion 206 has a first side portion 246 and a second side portion 248 opposite the first side portion 246. The maximum distance between the first side portion 242 of the elongated arms 210A-D and the second side portion 244 of the elongated arms 210A-D, respectively, is less than a maximum distance between the first side portion 246 of the body portion 206 and the second side portion 248 of the body portion 206. For example, the width B of the body portion 206 can be between 60 and 120 mm. The width A of the elongated arms 210A-D can be between 10 and 20 mm.

The frame member 204 is configured to help retain a shape of the support member 202 when the support member 202 is in the expanded configuration. The shape and structure of the body portion 206 in its expanded configuration is configured to support an anatomical structure. The frame member 204 has an expanded configuration and a collapsed configuration. The frame member 204 is biased in the expanded configuration. The frame member 204 is also configured to help maintain a shape defined by the elongated arms 210A, 210B, 210C, 210D such that the shape facilitates the retention of the support device 200 with respect to the anatomical structure. The frame member 204 is coupled to the support member 202, specifically, along a perimeter of the support device 202.

In one embodiment, the frame member 204 includes a shape memory alloy, such as, for example, nitinol, gold-cadmium, nickel-aluminum, manganese-copper, or the like. In some embodiments, the shape memory alloy can be temperature dependent. In other words, the frame member retains the collapsed configuration when in a cooled state, such as, for example, a temperature below body temperature and moves from the collapsed configuration to the expanded configuration when warmed to or above a set temperature, such as, for example, body temperature.

In the illustrated embodiment, the support member 202 is "I"-shaped, however, it should be understood that the support member can be any of a variety of shapes, including for example, "T"-shaped, "Z"-shaped, "X"-shaped, "L"-shaped and "H"-shaped.

The support member 202 includes multiple interwoven strands that collectively form a mesh. The frame member 204 can be a shape strand interwoven in the multiple interwoven strands. The mesh can be comprised of any known support materials, including for example, polyproylene, polyester, bioabsorbable materials (e.g., Vicryl, polydioxanone (suture) or PDS), or combinations of permanent and bioabsorbable materials. The mesh can have a knitted woven or non-woven matrix. The mesh can have a coating. For example, the mesh can be coated with an antimicrobial agent or pain medication.

In some embodiments, the frame member 204 is a strand from the mesh and includes a shape memory alloy.

In some embodiments, the support member 202 includes a single elongated arm 210A extending from the body portion 206.

In the illustrated embodiment, the support member 202 defines an axis C when the support member 202 is in the collapsed configuration as shown in FIG. 3. The axis C intersects a portion of the support member 202, specifically the body portion 206. The first elongated arm 210A, the second elongated arm 210C, the third elongated 210B and the fourth elongated member 210D each define an axis that is parallel to the axis C defined by the support member 202 when the support member 202 is in the collapsed configuration. For example, the first elongated arm 210A defines an axis E that is parallel to an axis F defined by the second elongated arm 210C. The axis E and the axis F are both parallel to the axis C. In some embodiments, the axis C is orthogonal to a plane defined by the support member 202 when the support member 202 is in the expanded configuration.

The support device 200 is configured to facilitate insertion into the pelvic region when the support member 202 is in the collapsed configuration. Specifically, the support member 202 is configured to be slidably inserted into a lumen of an insertion device when the support member 202 is in the collapsed configuration. More specifically, the first elongated arm 210A, the second elongated arm 210C, the third elongated arm 210B and the fourth elongated arm 210D are disposed in an adjacent arrangement when the support member 202 is in the collapsed configuration. In such a configuration, elongated arms 210A-D are each substantially parallel to one another. The elongate arms 210A-D are oriented such that the elongated arms 210A-D are disposed within a distal end portion of the lumen of the insertion device.

Figure 4:
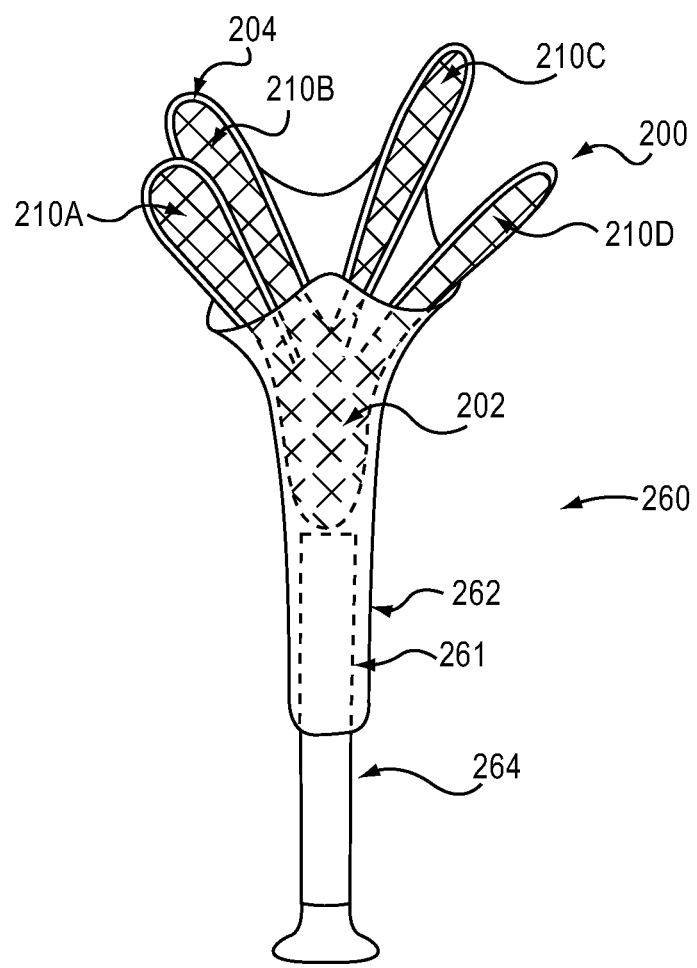
FIG. 4 is a perspective view of the support device of FIG. 2 shown partially disposed within an insertion device.

FIG. 4 is a side perspective view of the support device of FIG. 2 shown partially disposed within an insertion device 260. The insertion device 260 includes a delivery sleeve 262 and a pusher 264. The delivery sleeve 262 defines a lumen 261 extending therethough. In the illustrated embodiment, the delivery sleeve 262 is flared at one end to facilitate deployment of the support device 200. The design of the flare can vary depending on whether a pelvic floor mesh product such as the support device 200 of FIG. 2, or another medical device (such as an incontinence sling) is being deployed. In some embodiments, the insertion device can define an axis that is parallel to multiple axes defined by each of the elongated arms when the support member is in its collapsed configuration.

The support member 202 is configured to be slidably inserted into a lumen 261 of the insertion device 260 when the support member 202 is in the collapsed configuration. As illustrated, the adjacent arrangement of elongated arms 210A, 210B, 210C, 210D are oriented such that the elongated arms 210A, 210B, 210C, 210D are disposed within the flared end portion of the insertion device 260. Specifically, a distal end portion of each elongate arm 210A-D is disposed at the distal/flared end portion of the insertion device 260.

In one embodiment, the delivery sleeve 262 is made of a low friction material, such as, for example, polyethylene, polyproplylene, or the like, to facilitate insertion of the delivery sleeve 262 into a body of a patient. At the proximal end portion of the delivery sleeve 262, the pusher 264 is inserted into the lumen 261 and advanced distally within the lumen 261 to move the support device 200 out of the delivery sleeve 262 disposed, at least in part, within the body of the patient and into the desired anatomical location.

Figure 5:
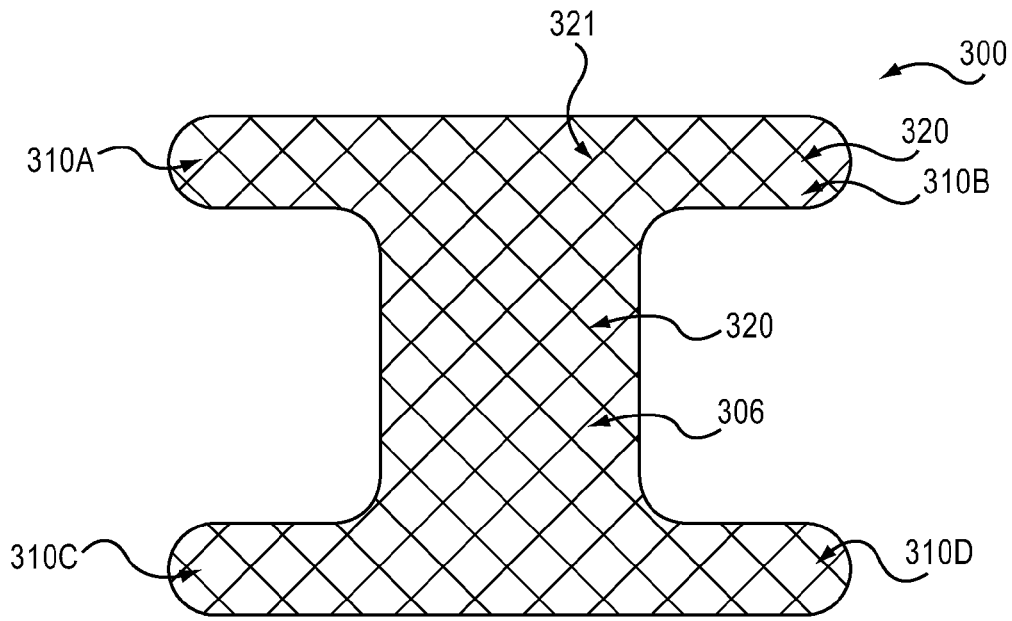
FIG. 5 is a top view of an embodiment of a support device in an expanded configuration.

FIG. 5 is a top view of an embodiment of a support device 300. The support device 300 includes multiple interwoven strands 320 that collectively define a shape. A shape strand 321 is interwoven into the multiple interwoven strands 320 and includes a shape memory alloy. The shape strand 321 is a frame member. The shape strand 321 has an expanded configuration and a collapsed configuration different from the expanded configuration. The shape strand 321 is biased in the expanded configuration. The shape strand 321 is configured to move from the collapsed configuration to the biased expanded configuration when in the collapsed configuration such that the multiple interwoven strands 320 collectively define the shape configured to support an anatomical structure. Specifically, the multiple interwoven strands 320 are configured to help support the anatomical structure. In an alternative embodiment, the shape strand 321 is coupled to the outer perimeter of the multiple interwoven strands 320.

The multiple interwoven strands 320 define a body portion 306 and multiple elongated arms 310 extending from the body portion 306. The body portion 306 is configured to support an anatomical structure when the shape strand 321 is in the biased expanded configuration. The elongated arms 310A-D are configured to help anchor the support device 300 with respect to the anatomical structure when the shape strand 321 is in the biased expanded configuration. The support device 300 is configured to be inserted into the pelvic region when it is in its collapsed configuration. Specifically, the elongated arms 310A-D can be disposed in an adjacent arrangement when the shape strand 321 is in the collapsed configuration to facilitate insertion into a body of a patient.

In some embodiments, the support device 300 includes a second strand that is interwoven into the multiple strands and includes a shape memory alloy. In some embodiments, the second strand is disposed along a perimeter of the plurality of interwoven strands.

The shape memory alloy can be, for example, nitinol, gold-cadmium, nickel-aluminum, manganese-copper, etc. In some embodiments, the shape memory alloy can be temperature dependent. In other words, the shape strand 321 retains the collapsed configuration when in a cooled state, such as, for example, below body temperature. The shape strand 321 is configured to move from the collapsed configuration to the expanded configuration when warmed to or above a set temperature, such as, for example, body temperature.

In the illustrated embodiment, the multiple interwoven strands 320 collectively form a mesh. The mesh can be comprised of any known support materials, including for example, polyproylene, polyester, bioabsorbable materials (e.g., Vicryl, polydioxanone (suture) or PDS), or combinations of permanent and bioabsorbable materials. The mesh can have a knitted woven or non-woven matrix. The mesh can have a coating. The mesh can be coated with an antimicrobial agent or pain medication.

Figure 6:
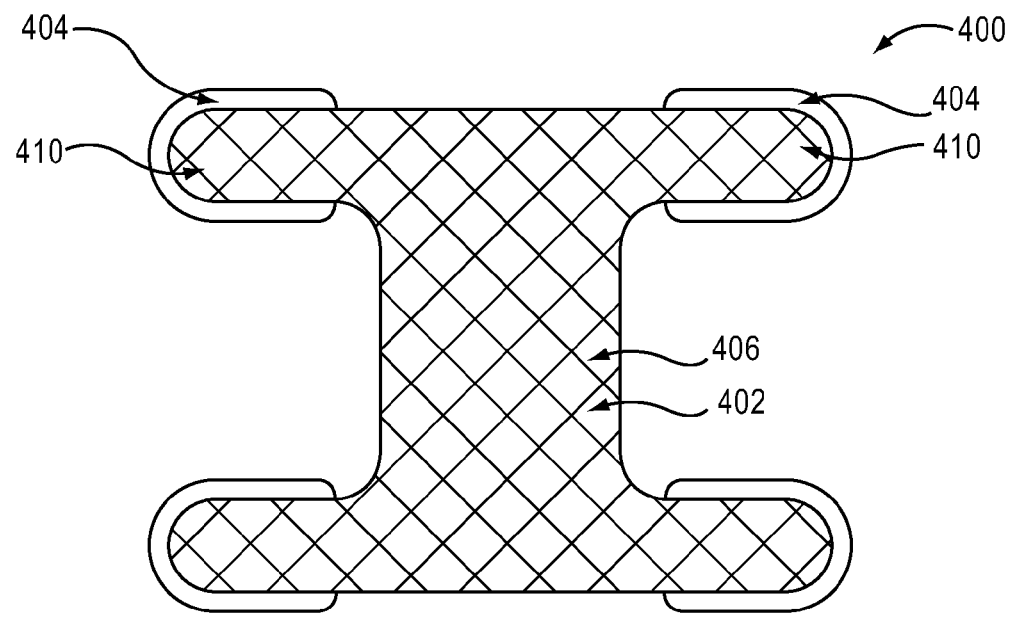
FIG. 6 is a top view of an embodiment of a support device.

FIG. 6 is a top view of an embodiment of a support device 400. The support device 400 includes a support member 402 and multiple frame members 404. The support member 402 includes a body portion 406 configured to help support a tissue located in the pelvic region. The support member 402 has multiple elongated arms 410 each extending from the body portion 406 and are each configured to help retain the support device 400 with respect to the tissue.

The frame members 404 are each configured to help maintain a shape defined by the elongated arms 410 the shape defined by each of the arms 410 facilitates the retention of the support device 400 with respect to the tissue. Each frame member 404 is coupled to at least a portion of a perimeter of each of the elongated arms 410, respectively. In one embodiment, each frame member 404 is comprised of a shape metal alloy.

The support device 400 has an expanded configuration and a collapsed configuration. The support device 400 is configured to support the tissue when in the expanded configuration. The support device 400 is configured to facilitate insertion into the pelvic floor region when in the collapsed configuration.

Figure 7:
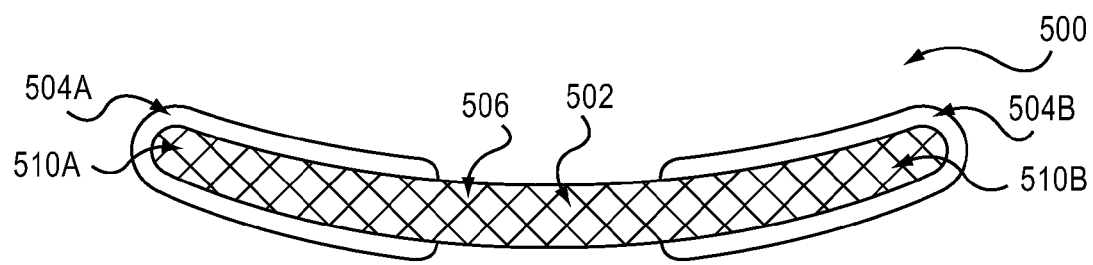
FIG. 7 is a top view of an embodiment of a support device.

FIG. 7 is a top view of an embodiment of a support device 500. The support device 500 includes an elongated support member 502 having a first end portion 510A and a second end portion 510B opposite the first end portion 510A. The support member 502 includes a body portion 506 configured to help support a tissue located in the pelvic region of a body of a patient. The body portion 506 is located between the first end portion 510A and the second end portion 510B. The first end portion 510A and the second end portion 510B are both configured to help retain the support member 502 with respect to an anatomical structure.

A first frame member 504A is coupled to at least a portion of a perimeter of the first end portion 510A. A second frame member 504B is coupled to at least a portion of a perimeter of the second end portion 510B. Each frame member 504 is configured to help maintain a shape defined by the first end portion 510A and the second end portion 510B such that the shape facilitates the retention of the support device 500 with respect to the anatomical structure.

In this embodiment, the support device 500 forms a sling. Specifically, the first end portion 510A and the second end portion 510B can be anchored at spaced locations while anchoring the body portion 506 between them to provide support for the anatomical structure. For example, the sling can be an incontinence sling.

Figure 8:
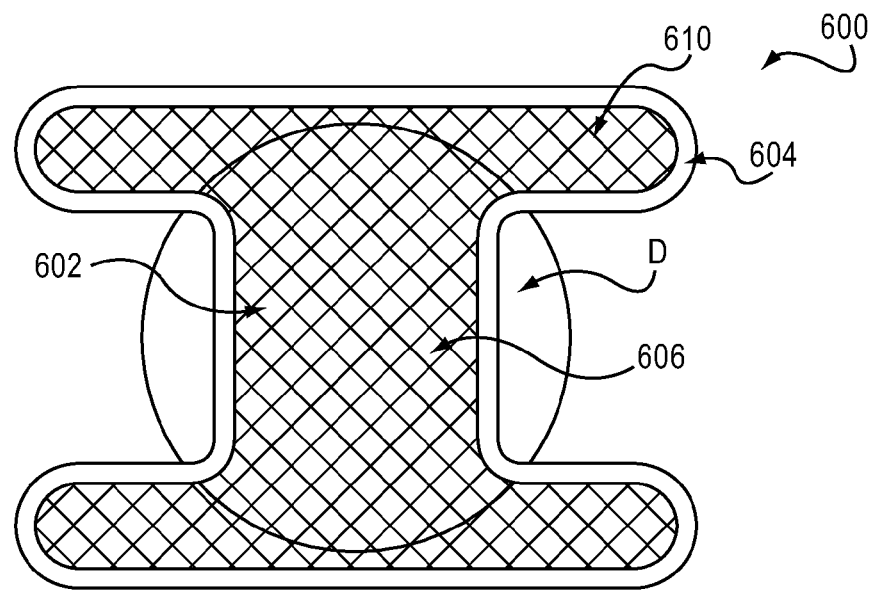
FIG. 8 is a bottom view of a support device shown schematically disposed within a body of a patient.

FIG. 8 is a bottom view of an embodiment of a support device schematically shown supporting an anatomical structure. A support device 600 is shown disposed within a pelvic region of a patient and includes a support member 602 and a frame member 604. A body portion 606 of the support member 602 provides support for an anatomical structure D. The anatomical structure D can be, for example, a bladder, a muscle, or another anatomical structure or tissue. Multiple elongated arms 610 extend from the body portion 606 and are each configured to help retain the support member 602 at a location with respect to the anatomical structure D. The frame member 604 is coupled to the support member 602 and is configured to help retain the shape illustrated. In this embodiment, the support device 600 is placed using the method described in the previous embodiment.

Figure 9:
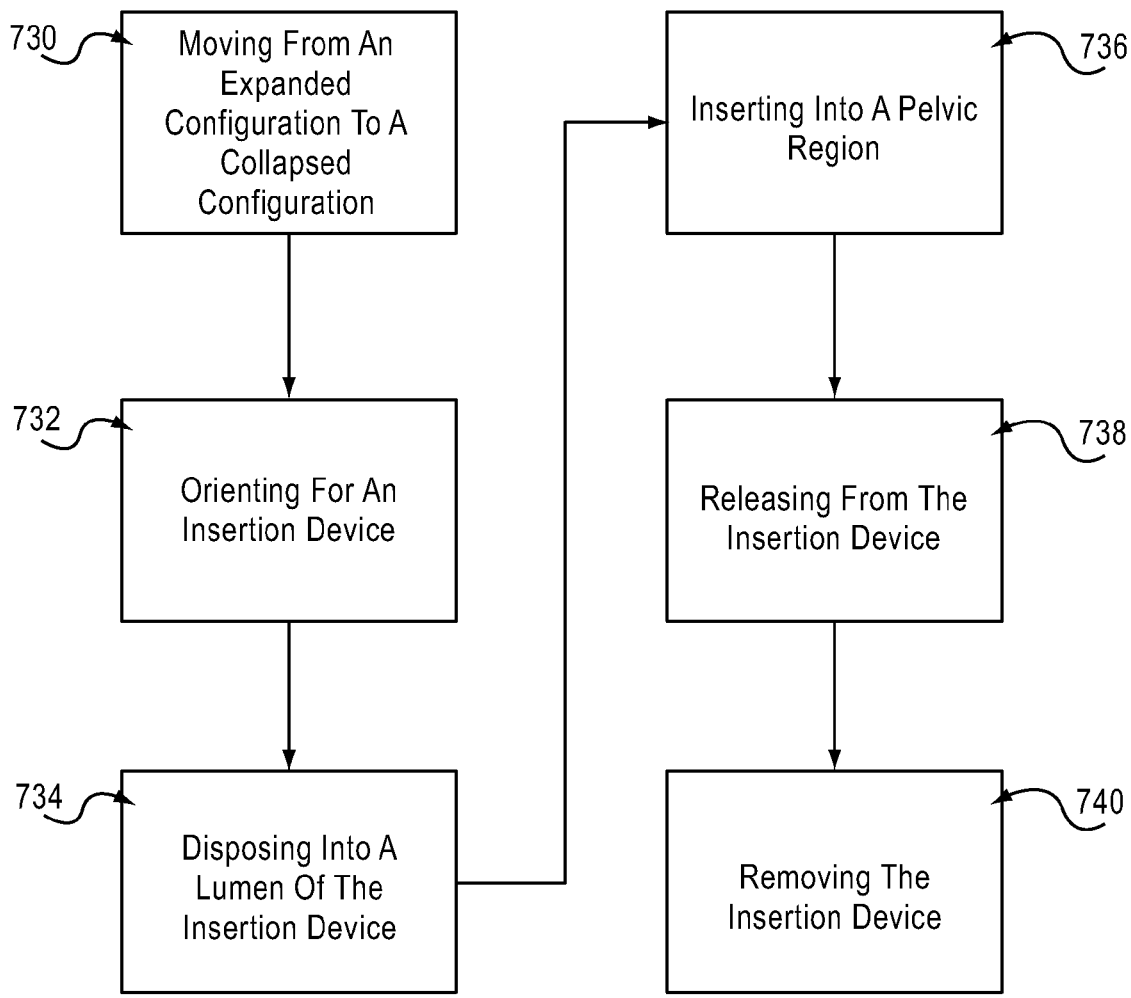
FIG. 9 is a flow chart illustrating a method of inserting an embodiment of the medical support device.

FIG. 9 is a flow chart showing a method of inserting an embodiment of the medical support device. At 730, a support device is moved from an expanded configuration to a collapsed configuration. The support device has multiple arms that are in an adjacent arrangement when the support device is in the collapsed configuration. At 732, the support device is oriented to facilitate insertion into a body of a patient from an insertion device when the support device is in the collapsed configuration. In other words, the support device is oriented such that the arms enter the body of the patient before a body portion of the support device. At 734, the support device is disposed into a lumen of the insertion device when the support device is in the collapsed configuration. At 736, a distal end portion of the support device is inserted into a pelvic region of a body of a patient. Specifically, a distal end portion of each of the arms are inserted at the same time (i.e., all at once) into the pelvic region. At 738, a pusher of the insertion device is moved from a proximal end portion of the insertion device towards a distal end of the insertion device to expel the support device from the lumen of the insertion device. The support device is configured to move from the collapsed configuration to the expanded configuration once it is expelled form the insertion device. The arms of the support device are configured to help retain the support device with respect to tissue in the pelvic region when the support device is in the expanded configuration. At 740, the insertion device is removed from the body of the patient.

The support device can be formed from any material or materials known in the art to be used in constructing support devices.

In one embodiment, a support device includes a support member having a body portion and an elongated arm extending from the body portion. The elongated arm has a width smaller than a width of the body portion of the support member. The body portion is configured to help support an anatomical structure located in a pelvic region of a patient. A frame member is coupled to the support member and is comprised of a shape memory alloy.

In some embodiments, the elongated arm is configured to help retain the support member at a location with respect to the anatomical structure. In some embodiments, the support member is a mesh. In some embodiments, the elongated arm is a first elongated arm. The support member includes a second elongated arm having a width smaller than a width of the body portion. In some embodiments, the support member has an "I"-shape.

In some embodiments, the elongated arm has a first side portion and a second side portion opposite the first side portion. The body portion has a first side portion and a second side portion opposite the first side portion. A distance between the first side portion of the elongated arm and the second side portion of the elongated arm is smaller than a distance between the first side portion of the body portion and the second side portion of the body portion.

In some embodiments, the support member includes a plurality of interwoven strands. The frame member is a strand interwoven in the plurality of interwoven strands.

In some embodiments, the support device has an expanded configuration and a collapsed configuration. The support device is configured to support tissue within the pelvic region when the support member is in the expanded configuration. The support device is configured to facilitate insertion into the pelvic region when the support member is in the collapsed configuration.

In some embodiments, the frame member has an expanded configuration and a collapsed configuration. The frame member is biased in the expanded configuration. In some embodiments, the frame member is coupled along at least a portion of a perimeter of the support member. In some embodiments, the frame member is coupled to the at least a portion of the elongated arm of the support member.

In another embodiment, a support device includes a support member having an expanded configuration and a collapsed configuration. The support device is configured to support tissue within the pelvic region when the support member is in the expanded configuration. The support member has a first side portion and a second side portion opposite the first side portion. A first elongated arm extends from the first side portion of the support member. A second elongated arm extends from the second side portion of the support member. The first elongated arm and the second elongated arm are disposed in an adjacent arrangement when the support member is in the collapsed configuration. A frame member is coupled to the support member.

In some embodiments, the frame member has an expanded configuration and a collapsed configuration. The frame member is biased in the expanded configuration.

In some embodiments, a third elongated arm extends from the first side portion. The first elongated arm, the second elongated arm and the third elongated arm are disposed in an adjacent arrangement when the support member is in the collapsed configuration.

In some embodiments, the frame member is comprised of a shape memory alloy.

In some embodiments, the support member is configured to be slidably inserted into a lumen of an insertion device when the support member is in the collapsed configuration.

In some embodiments, the first elongated arm is configured to help retain the support member at a location with respect to the tissue when the support member is in the expanded configuration.

In some embodiments, the support member defines an axis when the support member is in the collapsed configuration. The axis intersecting a portion of the support member. The first elongated arm and the second elongated arm each define an axis parallel to the axis defined by the support member when the support member is in the collapsed configuration.

In some embodiments, the support member defines an axis when the support member is in the collapsed configuration. The axis is orthogonal to a plane defined by the support member when the support member is in the expanded configuration.

In yet another embodiment, a support device includes a plurality of interwoven strands collectively defining a shape. A strand is interwoven into the plurality of interwoven strands. The strand includes a shape memory alloy. The strand has a biased first configuration and a second configuration different from the first configuration. The strand is configured to retain the plurality of interwoven strands in an expanded configuration such that the support device defines a shape configured to support a bodily structure.

In some embodiments, the plurality of interwoven strands are configured to help support the bodily structure. In some embodiments, the plurality of interwoven strands define an elongated arm configured to help anchor the support device with respect to the bodily structure when the strand is in the biased first configuration.

In some embodiments, the strand is a first strand. A second strand is interwoven into the plurality of interwoven strands and is comprised of a shape memory alloy. In some embodiments, the strand is a first strand. A second strand from the plurality of interwoven strands is comprised of a shape memory alloy and is disposed along a perimeter of the plurality of interwoven strands. In some embodiments, a frame member is coupled to the plurality of interwoven stands and is comprised of a shape memory alloy.

In yet another embodiment, a support device includes a support member that includes a body portion configured to help support a tissue located in the pelvic region. The support member has an elongated arm that extends from the body portion. A frame member is coupled to the elongated arm.

In some embodiments, the frame member is comprised of a shape memory alloy. In some embodiments, the elongated arm is configured to help retain the support device with respect to the tissue. In some embodiments, the frame member is coupled to at least a portion of a perimeter of the elongated arm.

In some embodiments, the frame member is a first frame member and the elongated arm is a first elongated arm. The first frame member is coupled to at least a portion of a perimeter of the first elongated arm. A second elongated arm extends from the body portion. A second frame member is coupled to at least a portion of a perimeter of the second elongated arm.

In some embodiments, the support device has an expanded configuration and a collapsed configuration. The support device is configured to support the tissue when in the expanded configuration. The support device is configured to facilitate insertion into the pelvic region when in the collapsed configuration.

In yet another embodiment, a method of inserting a support device that has a plurality of arms. The plurality of arms are in an adjacent arrangement when the support device is in a collapsed configuration. The method includes inserting the support device into a pelvic region of a body of a patient and releasing the support device from a lumen of an insertion device. The support device is configured to move from the collapsed configuration to an expanded configuration.

In some embodiments, the inserting the support device includes inserting an end portion of each of the plurality of arms at the same time.

In some embodiments, each arm from the plurality of arms is configured to help retain the support device with respect to tissue in the pelvic region when the support device is in the expanded configuration.

In some embodiments, the method includes moving the support device from the expanded configuration to the collapsed configuration before the inserting the support device.

In some embodiments, the method includes disposing the support device into the lumen of the insertion device when the support device is in the collapsed configuration before the inserting the support device.

In some embodiments, the releasing the support device includes moving a pusher of the insertion device from a proximal end portion of the insertion device towards a distal end of the insertion device.

In some embodiments, the method includes removing the insertion device from the body of the patient after the releasing.

In some embodiments, the method includes orienting the support device such that the plurality of arms are disposed at a distal end of an insertion device when the support device is in the collapsed configuration.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The previous description of the embodiments is provided to enable any person skilled in the art to make and use the invention. While the invention has been particularly shown and described with reference to embodiments thereof, it will be understood by those skilled in the art that various changes in form and details may be made. For example, a support device can include various combinations and sub-combinations of the various embodiments described herein.

What is claimed is:

1. A support device, comprising:
   a support member having a body portion and a first elongated arm extending from a side portion of the body portion in a first direction and a second elongated arm extending from the side portion of the body portion in a second direction, the first direction being parallel to the second direction, the first elongated arm having a width smaller than a width of the body portion of the support member, the body portion being configured to help support an anatomical structure located in a pelvic region of a patient, and a frame member, the frame member being coupled to the first elongated arm and to the second elongated arm, the frame member extending along a length of the first elongated arm, the frame member being comprised of a shape memory alloy, wherein the support member includes a plurality of interwoven strands and the frame member is a strand interwoven in the plurality of interwoven strands.

2. The support device of claim 1, wherein the support member is a mesh.

3. The support device of claim 1, wherein the first elongated arm has a first side portion and a second side portion opposite the first side portion, the body portion has a first side portion and a second side portion opposite the first side portion, a distance between the first side portion of the first elongated arm and the second side portion of the first elongated arm being smaller than a distance between the first side portion of the body portion and the second side portion of the body portion.

4. The support device of claim 1, wherein the frame member has an expanded configuration and a collapsed configuration, the frame member being biased in the expanded configuration.

5. The support device of claim 1, wherein the frame member is coupled to the body portion of the support member and includes a portion that extends from the body portion in a direction parallel to the first direction.

6. A support device, comprising:
a support member having an expanded configuration and a collapsed configuration, the support device being configured to support tissue within the pelvic region when the support member is in the expanded configuration, the support member having a first side portion and a second side portion opposite the first side portion, a first elongated arm and a second elongated arm extending from the first side portion of the support member, and a third elongated arm and a fourth elongated arm extending from the second side portion of the support member, the first elongated arm having a width smaller than a width of the support member, the first elongated arm and the third elongated arm being disposed in an adjacent arrangement when the support member is in the collapsed configuration, the support member including a mesh material, the first elongated arm including a mesh material; and a frame member, the frame member being coupled to the first elongated arm, to the second elongated arm, to the third elongated arm, and to the fourth elongated arm.

7. The apparatus of claim 6, wherein the frame member has an expanded configuration and a collapsed configuration, the frame member being biased in the expanded configuration.

8. The support device of claim 6, wherein:
the support member defines an axis when the support member is in the collapsed configuration, the axis intersecting a portion of the support member; and
the first elongated arm and the third elongated arm each define an axis parallel to the axis defined by the support member when the support member is in the collapsed configuration.

9. The support device of claim 6, wherein the support member defines an axis when the support member is in the collapsed configuration, the axis being orthogonal to a plane defined by the support member when the support member is in the expanded configuration.

10. A support device, comprising:
a plurality of interwoven strands collectively defining a shape, the shape including a body portion, a first arm portion extending from the body portion, a second arm portion extending from the body portion, a third arm portion extending from the body portion, and a fourth arm portion extending from the body portion, the first arm portion including the plurality of interwoven stands; and a strand interwoven into the plurality of interwoven strands, the strand including a shape memory alloy, the strand having a biased first configuration and a second configuration different from the first configuration, the strand being configured to retain the plurality of interwoven strands in an expanded configuration such that the support device defines a shape configured to support a bodily structure, the strand extending from the first arm portion to the second arm portion, from the second arm portion to the third arm portion, and from the third arm portion to the fourth arm portion.

11. The support device of claim 10, wherein the strand is a first strand, the support device further comprising:
a second strand interwoven into the plurality of interwoven strands and being comprised of a shape memory alloy.

12. The support device of claim 10, wherein the strand is a first strand, the support device further comprising:
a second strand from the plurality of interwoven strands being comprised of a shape memory alloy and being disposed along a perimeter of the plurality of interwoven strands.

13. The support device of claim 10, further comprising a frame member coupled to the plurality of interwoven stands and being comprised of a shape memory alloy.

14. A support device, comprising:
a support member including a body portion configured to help support a tissue located in a pelvic region, the support member having a first elongated arm extending from the body portion, a second elongated arm extending from the body portion, a third elongated arm extending from the body portion, and a fourth elongated arm extending from the body portion, the body portion and the first elongated arm being formed of a mesh, and a frame member, the frame member being coupled to the first elongated arm, to the second elongated arm, to the third elongated arm, and to the fourth elongated arm.

15. A method of inserting a support device having a plurality of arms including a first elongated arm, second elongated arm, third elongated arm, and fourth elongated arm, each of the plurality of arms having a mesh portion, the plurality of arms being in an adjacent arrangement when the support device is in a collapsed configuration, the support device including a frame portion, the frame portion being coupled to the first elongated arm, to the second elongated arm, to the third elongated arm, and to the fourth elongated arm the frame portion extending along a length of each of the plurality of arms, comprising:
inserting an insertion device defining a lumen into a pelvic region of a body of a patient, at least a portion of the support device being disposed within the lumen; and
releasing the support device from the lumen of the insertion device, the support device being configured to move from the collapsed configuration to an expanded configuration.

16. The method of claim 15, further comprising moving the support device from the expanded configuration to the collapsed configuration before the inserting the insertion device.

17. The method of claim 15, further comprising disposing the support device into the lumen of the insertion device when the support device is in the collapsed configuration before inserting the insertion device.

18. The method of claim 15, wherein releasing the support device includes moving a pusher of the insertion device from a proximal end portion of the insertion device towards a distal end of the insertion device.

* * * * *